United States Patent [19]

Debat

[11] 4,113,875

[45] Sep. 12, 1978

[54] COMPOSITIONS FOR THE TREATMENT OF DISORDERS OF THE PROSTATE GLAND

[75] Inventor: Jacques Debat, Paris, France

[73] Assignee: Institut de Recherches Chimiques et Biologiques Appliquees, France

[21] Appl. No.: 673,915

[22] Filed: Apr. 5, 1976

Related U.S. Application Data

[62] Division of Ser. No. 557,369, Mar. 11, 1975, abandoned.

[30] Foreign Application Priority Data

Mar. 11, 1974 [GB] United Kingdom ............... 10683/74

[51] Int. Cl.² .......................................... A61K 31/335
[52] U.S. Cl. ................................................... 424/278
[58] Field of Search ........................................ 424/278

[56] References Cited

FOREIGN PATENT DOCUMENTS 1,111,206  6/1966  United Kingdom ................ 260/348 R

*Primary Examiner*—Sam Rosen
*Attorney, Agent, or Firm*—Bucknam and Archer

[57] ABSTRACT

The invention relates to novel compounds in the form of epoxy alkanes corresponding to the formula

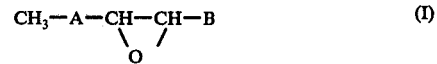

(I)

in which B is H or $CH_3$ and A represents a hydrocarbon radical containing at least 15 carbon atoms.

These epoxy alkanes are suitable for therapeutic application, especially in the treatment of secretory disorders of the prostate gland, more especially prostate adenoma.

10 Claims, No Drawings

COMPOSITIONS FOR THE TREATMENT OF DISORDERS OF THE PROSTATE GLAND

This is a division of application Ser. No. 557,369 filed Mar. 11, 1975, now abandoned.

This invention relates to novel epoxides corresponding to formula I below. These compounds are suitable for therapeutic application, especially in the treatment of secretory disorders of the prostate gland and more especially in the treatment of prostate adenoma.

In British patent application No. 40568/73 filed Aug. 29, 1973, it was shown that higher alkanols with 16 or more carbon atoms are suitable for therapeutic application in the treatment of secretory disorders of the prostate gland, especially prostate adenoma. It has not been found that 1,2- and 2,3-epoxy alkanes corresponding to the general formula

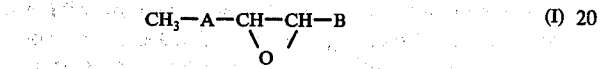

in which B is H or $CH_3$ and A is a hydrocarbon radical containing at least 15 carbon atoms, and their geometric isomers are as active as the abovementioned alkanols.

In order to complete acknowledgement of the prior art, it is pointed out that, although the 1,2- and 2,3-epoxy alkanes of formula I are new and show interesting therapeutic properties, only a single $C_{19}$ epoxy alkane is already known. The compound in question, namely cis-7,8-epoxy-2-methyloctadecane, is a pheromone found in lepidoptera. It is emitted by females of *Porthetria dispar* to attract males with the object of intraspecific copulation. This pheromone is a laboratory curiosity. After extraction, its structure was established by BEROZA in Journal of Association of Officinal Analytical Chemists (1971), 54, 251, and then confirmed by synthesis by EITER in Angew. Chem. Internat. (English Edition), (1972), 11, 60.

In accordance with the definition of formula I, the invention relates to 1,2-epoxy alkanes with 18 or more carbon atoms and their geometric isomers, and 2,3-epoxy alkanes with 19 or more carbon atoms and their geometric isomers.

In the context of the invention, the "hydrocarbon radical" A is a straight-chain or branched-chain hydrocarbon radical with at least 15 carbon atoms. As illustratd hereinafter, the preferred hydrocarbon radicals are those with a linear chain, in which case A represents in particular $(CH_2)_{15}$, $(CH_2)_{16}$, $(CH_2)_{17}$, $(CH_2)_{18}$, $(CH_2)_{19}$ and $(CH_2)_{20}$. The lower limit of 15 carbon atoms was determined by a statistical activity study, as will be seen hereinafter.

The compounds of formula I are prepared in known manner by reacting a corresponding alkene with a peracid. The method used comprises reacting 1 mol of an alkene corresponding to the formula

in which A and B are as defined above, with more than 1 mol of peracid at ambient temperature (15°-25° C).

Peracids which may be used for the purpose include, in particular, peracetic acid, perbenzoic acid, perphthalic acid and metachloroperbenzoic acid. Although these peracids are equivalent, it has been found that the use of metachloroperbenzoic acid is more economic from the commercial point of view, especially in regard to the purity of the end product. The reason why it is more economic to use metachloroperbenzoic acid is that the metachlorobenzoic acid formed during the reaction is easier to remove than the other acids.

In order to carry out this reaction, 1.1 mol of metachloroperbenzoic acid is reacted with 1 mol of alkene II in an inert solvent, such as methylene chloride.

The 1-alkenes of formula II are commercially available products. The 2-alkenes of formula II may be prepared in particular a) from the corresponding 2-alkanols by treatment with $H_2SO_4$ or b) by reacting an organomagnesium compound of formula III with 1-chloro-2-butene (formula IV) in accordance with the following scheme:

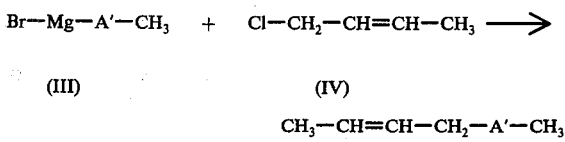

where A' is a hydrocarbon radical containing at least 14 carbon atoms.

Methods A and B described below each represent one method of preparing 2,3-epoxy eicosane from 2-eicosene by oxidation with metachloroperbenzoic acid (Method A) and with peracetic acid (Method B). Methods C and D relate to the preparation of a starting alkene, namely 2-eicosene.

Method A 6 g of 2-eicosene are dissolved in 100 cc of methylene chloride and the resulting solution is introduced into a flask equipped with a condenser and a stirrer (if necessary, this flask may be immersed in a cooling or heating bath).

4 g of metachloroperbenzoic acid, i.e. a molar excess of approximately 10% relative to the stoichiometric quantity, are progressively introduced (over a period of approximately 30 minutes). The mixture is stirred and kept at ambient temperature (15°-25° C) during the addition by means of a stream of water, and is then left standing at ambient temperature for about 10 hours. The mixture is then heated under reflux for 2 hours in order to destroy the peracid.

A large quantity of the metachlorobenzoic acid formed precipitates after cooling. It is eliminated by filtration. The chloromethylene solution is washed first with 100 cc of sodium sulphate (100 g/l) and then with 100 cc of sodium bicarbonate (100 g/l) and finally with water until it has a pH-value above 6. The organic solution is dried over calcium chloride and then distilled to remove the methylene chloride. 4.8 g of product are obtained, corresponding to a crude yield of 76%.

The product is purified by column chromatography. 100 g of chromatography-grade silica suspended in petroleum ether are introduced into a 3.5 cm diameter glass column. After the gel has been introduced, the crude product obtained is introduced at the head of the column after having been dissolved in a minimal volume of petroleum ether. The column is then washed with petroleum ether, which enables 0.2 g of product to be removed to be recovered in 1 liter of washing solvent. Elution is then carried out with a 90 : 10 mixture of petroleum ether and diethylether. 4.5 g of 2,3-epoxy eicosane are recovered from 500 ml of the eluate. Mp: 40° C, bp $_{15mm}$ Hg : 200°-210° C.

Method B 7 g of 2-eicosene are dissolved in 20 g of peracetic acid. The ethylenic function is oxidised into epoxide in the absence of heat. The acetic acid formed is neutralised in 10 ml of water by the addition of 1N NaOH. The aqueous solution thus obtained is extracted with ether. Removal of the ether leaves 6 g of 2,3-epoxy eicosane which is purified in the same way as described above. Mp: 40° C, bp $_{15}$mm Hg : 200°–210° C.

Method C 35 g of a 60% by weight solution of sulphuric acid are introduced into a 100 ml flask equipped with a condenser and stirrer and heated in an oil bath. 7 g of 2-eicosanol (0.0234 mol) are introduced into the flask, followed by heating under reflux (100°–110° C) for 16 hours.

After cooling, the reaction product is extracted with 200 ml of chloroform, the chloroformic solution washed twice with 150 ml of sodium carbonate (100 g/l) and then several times with water until a pH value above 6 is obtained. the chloroformic solution is dried over calcium chloride, the chloroform is removed by distillation and, finally, the residue is distilled at around 180° C/15 mm Hg. 6 g of 2-eicosene are obtained, corresponding to a yield of 85%.

Method D 61 g of 1-bromohexadecane are dissolved in 100 ml of dry ether. 4.86 g of magnesium turnings are then introduced into the flask. These quantities are stoichiometric.

The Grignard reaction is initiated in the usual way by adding an iodine crystal. Once started, it is externally controlled by means of an ice bath and held under reflux. It stops spontaneously after a few minutes.

On completion of the operation, a solution containing 18 g of 1-chloro-2-butene in 20 ml of dry ether is added in the absence of heat. The exothermic reaction is held under natural reflux which stops after about 15 minutes.

The cooled solution is washed with water containing an excess of hydrochloric acid in order to dissolve the magnesia formed. The ethereal solution is recovered by decantation and then dried. The ethylenic compound, namely 2-eicosene, is obtained in a quantitative yield. It is purified by distillation in vacuo at 160° C/1 mm Hg.

After the heads and tails have been removed, 7 g of product are obtained, its composition and purity being readily verified by N.M.R.

A few epoxy alkanes corresponding to formula I and two comparison products, A-1 and A-2, are shown in Table I below, all these products having been prepared by Method A. The 2,3-epoxy eicosane prepared by methods A and B is also shown in this table (Example 4).

It is recommended to use therapeutic compositions containing, in association with a physiologically acceptable excipient, a therapeutically effective quantity of at least one compound corresponding to formula I.

Any physiologically acceptable liquid or solid vehicles may be used for preparing these therapeutic compositions containing the higher epoxy alkanes according to the invention. Solid preparations include, in particular, powders, tablets, granules, capsules, dragees and suppositories.

The solid vehicle which may be used contains one or more substances acting as diluent, perfume, solubiliser, lubricant, binder, surfactant or disintegration agent in the case of tablets. The solid vehicle may also contain one or more encapsulating substances. In powder form, the active compound is associated with a finely divided solid vehicle. In tablets, the active compound is mixed in suitable proportions with a vehicle having the requisite binding properties. The powders and tablets contain from 1 to 90% by weight of active ingredient. Suitable solid vehicles are, in particular, magnesium carbonate, magnesium stearate, talcum saccharose, glucose, lactose, pectin, dextrin, starch, gelatin, tragacanth, methyl cellulose, sodium carboxy methyl cellulose, low-melting waxes and cocoa butter.

Liquid preparations include solutions, suspensions and emulsions. In this case, the vehicle may be an aqueous solution of polyethylene glycol or polypropylene glycol on the one hand and oil, especially olive oil on the other hand.

The aqueous suspensions for oral administration are prepared by dispersing the finely divided active compound in water with a viscous substance, a natural or synthetic gum, a resin, etc., for example with gum arabic, an ion-exchange resin, methyl cellulose, carboxy methyl cellulose or any other well known suspending agent. The results of pharmacological tests carried out with the compounds according to the invention are summarised in the following.

The histological changes produced in the epithelium of adult rats were examined. It was found that the compounds according to the invention were capable of stimulating the function of the prostate gland in adult rats orally treated with very small doses over periods ranging from 15 days to 3 months. A significant improvement was then observed, for example with a dose of 0.5 mg per kg of body weight per day in the case of the products of Examples 1 to 6.

Technique

The epoxy alkane to be tested in an excipient, for example olive oil, was administered daily in the dose indicated for the period indicated to adult rats aged approximately 9 months.

Control rats are only given the excipient.

In the test described, the animals were treated 6 days a week for 7 weeks. Each epoxy alkane was administered in solution in a volume of 0.1 ml/100 g of body weight, i.e. in a concentration of 0.5 g of product per litre of oil.

On completion of the test, the control animals and treated animals were killed, the ventral part of their prostate glands removed, fixed with alcohol and then histologically examined.

The state of sections cut from the periphery of the prostate glands is noted in accordance with the following schedule:

Epithelium + 1

Enlargement of the peripheral epithelium of the central glands assuming a cubic appearance and occupying more than the outer half of the surface of the prostate gland.

Epithelium + 2

Enlargement of the epithelium, assuming a cylindrical appearance throughout.

Epithelium + 3

Epithelium identical throughout with that of the peripheral glands.

Epithelium + 4

Papillary hyperplasia of the epithelium with hypersecretion (this "stage" was not observed in the tests conducted).

Table II below shows the results relating to the ventral prostates examined after killing of the controls and treated animals which had been given the epoxy alkanes of Examples 1 to 6 and comparison examples A-1 and A-2 in the doses indicated.

Table II also shows the results of a statistical study carried out by the "chi 2" ($\chi^2$) and the EPP index method. The "chi 2" method enables the probability factor "p" to be deduced. The EPP index (examination of the periphery of the prostate gland) is defined as the ratio of the sum of all the animals classed "epithelium 1+" bearing the coefficient 1, "epithelium 2+" bearing the coefficient 2 and "epithelium 3+" bearing the coefficient 3 by the number of animals, ... enables the statistical study to be confirmed. As indicated in Table II, there is no activity when EPP is less than 1.80, whereas activity is found at the level of the prostate gland where EPP is greater than or equal to 1.80.

In conclusion, examination of the ventral part cut out from the periphery of the prostate glands shows that comparison products A-1 and A-2, which respectively contain a $C_9$ and $C_{13}$ hydrocarbon radical, are inactive because they give a result similar to the control group. This absence of activity in products A-1 and A-2 is confirmed by the statistical study in relation to the controls in accordance with the "chi 2" method. In addition, in the series of epoxy alkanes corresponding to formula I, the activity of the level of the prostate glands begins to appear when the hydrocarbon radical A contains at least 15 carbon atoms, as is the case with the compound of Example 1, in whose case a significant difference is noted in relation to the controls. The compounds of Examples 2 to 6 are highly active.

It is apparent from the foregoing that the 1,2-epoxy alkanes of formula I are active when they contain in their molecule at least 18 carbon atoms, and that the 2,3-epoxy alkanes of formula I are active when they contain at least 19 carbon atoms in their molecule.

TABLE I

| Example (Code No.) | Developed Formula | | Empirical Formula | Elemental Analysis | | | | Melting Point °C | Boiling Point at 15 mm Hg (°C) |
|---|---|---|---|---|---|---|---|---|---|
| | | | | C calculated | found | H calculated | found | | |
| A-1 | $CH_3-(CH_2)_9-CH-CH_2$ \ O / | 1,2-epoxy-dodecane | $C_{12}H_{24}O$ 184.31 | 78.19 | 77.8 | 13.13 | 13.0 | liquid at ambient temperature | 118–120 |
| A-2 | $CH_3-(CH_2)_{13}-CH-CH_2$ \ O / | 1,2-epoxy-hexadecane | $C_{16}H_{32}O$ 240.42 | 79.93 | 79.43 | 13.42 | 13.1 | recrystallises slowly | 171–173 |
| 1 | $CH_3-(CH_2)_{15}-CH-CH_2$ \ O / | 1,2-epoxy-octadecane | $C_{18}H_{36}O$ 268.47 | 80.52 | 80.5 | 13.52 | 13.1 | recrystallises slowly | 196–199 |
| 2 | $CH_3-(CH_2)_{17}-CH-CH_2$ \ O / | 1,2-epoxy-eicosane | $C_{20}H_{40}O$ 296.52 | 81.01 | 80.6 | 13.60 | 13.3 | 42 | 200–207 |
| 3 | $CH_3-(CH_2)_{19}-CH-CH_2$ \ O / | 1,2-epoxy-docosane | $C_{22}H_{44}O$ 324.57 | 81.41 | 81.2 | 13.66 | 13.3 | 46–47 | 205–210 |
| 4 | $CH_3-(CH_2)_{16}-CH-CH-CH_3$ \ O / | 2,3-epoxy-eicosane | $C_{20}H_{40}O$ 296 | 81.01 | 81.0 | 13.60 | 13.5 | 40 | 200–210 |
| (T-20) 5 | $CH_3-(CH_2)_{18}-CH-CH-CH_3$ \ O / | 2,3-epoxy-docosane | $C_{22}H_{44}O$ 324 | 81.41 | 81.4 | 13.66 | 13.5 | 48–50 | 205–215 |
| (T-22) 6 | $CH_3-(CH_2)_{20}-CH-CH-CH_3$ \ O / | 2,3-epoxy-tetracosane | $C_{24}H_{48}O$ 352.62 | 81.74 | 81.5 | 13.72 | 13.6 | 52 | 210–220 |
| (T-24) | | | | | | | | | |

TABLE II

| Product (Code No.) | Number of animals | Activity | | | Comparison with controls(a) | | E.P.P. (b) | Remarks |
|---|---|---|---|---|---|---|---|---|
| | | Epithelium 1+ | Epithelium 2+ | Epithelium 3+ | $\chi^2$ | p | | |
| Control Group | 40 | 29 | 8 | 3 | | | 1.35 | |
| A-1 | 20 | 13 | 7 | 0 | 2.807 | n.s(d) | 1.35 | quoted for comparison (c) |
| A-2 | 19 | 11 | 7 | 1 | 1.937 | n.s(d) | 1.47 | quoted for comparison (c) |
| 1 | 20 | 7 | 10 | 3 | 7.875 | between 0.05 and 0.02 | 1.80 | beginning of activity |
| 2 | 20 | 7 | 8 | 5 | 8.187 | between 0.02 and 0.01 | 1.90 | active |
| 3 | 20 | 5 | 9 | 6 | 12.749 | between 0.01 and | 2.05 | active |

TABLE II-continued

| Product (Code No.) | Number of animals | Activity Epithelium 1+ | Epithelium 2+ | Epithelium 3+ | Comparison with controls(a) $\chi^2$ | p | E.P.P. (b) | Remarks |
|---|---|---|---|---|---|---|---|---|
| 4(T-20) | 20 | 5 | 11 | 4 | 12.252 | between 0.01 and 0.001 | 1.95 | active |
| 5(T-22) | 20 | 6 | 10 | 4 | 9.914 | between 0.01 and 0.001 | 1.90 | active |
| 6(T-24) | 20 | 4 | 10 | 6 | 15.181 | above 0.001 | 2.10 | active |

(a): statistical study;

(b): E.P.P. = $\dfrac{1 \times \text{(epithelium 1+)} + 2 \times \text{(epithelium 2+)} + 3 \times \text{(epithelium 3+)}}{\text{number of animals examined}}$ (c): statistically inactive;

(d) n.s. = not significant

What is claimed is:

1. A therapeutic composition suitable for use in the treatment of prostate adenoma which comprises a therapeutically active amount of at least one aliphatic epoxy compound, which is selected from the group consisting of
   (a) epoxy alkanes corresponding to the general formula $$CH_3-A-CH-CH-B \qquad (I)$$
$$\diagdown O \diagup$$

in which B is H or $CH_3$ and A represents a hydrocarbon radical containing between 15 and 20 carbon atoms, and
   (b) their geometric isomers, and a physiologically acceptable excipient.

2. The composition according to claim 1 wherein the epoxy-alkane has the general formula

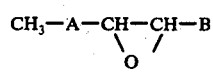

$$CH_3-A-CH-CH-B \qquad (I)$$
$$\diagdown O \diagup$$

in which B is H or $CH_3$ and A is a straight-chain hydrocarbon radical containing 15 and 20 carbon atoms.

3. A composition according to claim 1 wherein in the epoxy-alkane B is H.

4. A composition according to claim 1 wherein in the epoxy-alkane A is $(CH_2)_{15}$, $(CH_2)_{16}$, $(CH_2)_{17}$, $(CH_2)_{18}$, $(CH_2)_{19}$, or $(CH_2)_{20}$.

5. A composition according to claim 1 wherein the epoxy-alkane is 1,2-epoxy octadecane.

6. A composition according to claim 1 wherein the epoxy-alkane is 1,2-epoxy-eicosane.

7. A composition according to claim 1 wherein the epoxy-alkane is 1,2-epoxy-docosane.

8. A composition according to claim 1 wherein the epoxy-alkane is 2,3-epoxy-eicosane.

9. A composition according to claim 1 wherein the epoxy-alkane is 2,3-epoxy-docosane.

10. A composition according to claim 1 wherein the epoxy-alkane is 2,3-epoxy-tetracosane.

* * * * *